United States Patent [19]

MacEachern

[11] Patent Number: 5,758,657
[45] Date of Patent: Jun. 2, 1998

[54] PRESSURE TRANSDUCER POSITIONING SYSTEM AND METHOD

[75] Inventor: A. Walter MacEachern, Woburn, Mass.

[73] Assignee: Gatron Corporation, Woburn, Mass.

[21] Appl. No.: 198,838

[22] Filed: Feb. 18, 1994

[51] Int. Cl.⁶ .................................................. A61B 5/02
[52] U.S. Cl. .............................. 128/673; 128/672; 33/379
[58] Field of Search ......................... 128/672, 673, 128/674, 675, 748; 33/379

[56] References Cited

U.S. PATENT DOCUMENTS

| | | | |
|---|---|---|---|
| 3,495,585 | 2/1970 | Halligan et al. | 128/674 |
| 3,590,818 | 7/1971 | Lemole | 128/674 |
| 3,693,612 | 9/1972 | Donahoe et al. | 128/674 |
| 4,539,998 | 9/1985 | McCord et al. | 128/675 |
| 4,545,389 | 10/1985 | Schaberg et al. | 128/748 |
| 4,546,774 | 10/1985 | Hought | 128/673 |
| 4,557,269 | 12/1985 | Reynolds et al. | 128/675 |
| 4,576,181 | 3/1986 | Wallace et al. | 128/675 |
| 4,589,287 | 5/1986 | Dickens | 73/727 |
| 4,638,811 | 1/1987 | Bisere et al. | 128/673 |
| 4,669,484 | 6/1987 | Masters | 128/674 |
| 4,679,567 | 7/1987 | Hanlon et al. | 128/675 |
| 4,697,710 | 10/1987 | Dickens et al. | 128/672 |
| 4,776,343 | 10/1988 | Hubbard et al. | 128/675 |
| 4,779,626 | 10/1988 | Peel et al. | 128/673 |
| 5,168,633 | 12/1992 | Harrison et al. | 128/673 |
| 5,280,789 | 1/1994 | Potts | 128/672 |

*Primary Examiner*—Lee S. Cohen
*Attorney, Agent, or Firm*—Hamilton, Brook, Smith & Reynolds, P.C.

[57] ABSTRACT

An optical system for positioning a pressure transducer relative to a patient to provide for accurate measurement of bodily fluids within the patient. A light source such as a laser is used to direct light onto a specified location on the human body to accurately identify the elevation of the transducer relative to the specified location to provide an absolute measurement of fluid pressure.

27 Claims, 4 Drawing Sheets

PRESSURE TRANSDUCER POSITIONING SYSTEM AND METHOD

BACKGROUND OF THE INVENTION

During medical procedures as well as pre- and post-operation, monitoring of fluid pressure within the patient is necessary in conjunction with the assessment of the patient care and treatment. The fluid pressure monitoring is most commonly arterial blood pressure, but knowledge concerning intracranial fluid pressure, venous pressure, and intra-heart pressure also can provide important insight into a patient's current condition. One of the most effective devices for these types of measurements is a pressure transducer directly communicating with the particular bodily fluid of interest. Typically, the patient is catheterized and a tube, usually containing saline fluid, provides a fluid communication path between the bodily fluid and the pressure transducer. Then, the electrical impulses generated by the pressure transducer, which are a function of the bodily fluid pressure, are displayed by a monitor or other display device to monitor specific body functions.

The transducer housing is usually mounted in close proximity to the patient on an I.V. pole with an I.V. bag providing the saline solution. If the user desires only information regarding the dynamics of the bodily fluid pressure, then the pressure transducer can be mounted almost anywhere vertically on the I.V. pole. If the user, however, desires to monitor the absolute pressure of the bodily fluid, then the pressure transducer must be mounted in a fixed relationship to the patient. For example, if absolute arterial pressure is to be monitored, then the pressure transducer must be mounted approximately at the level of the heart.

A continuing need exists to provide accurate reproducible methods for monitoring hemodynamic pressure. Variations in the position of the sensor system relative to the patient continue to result in improper assessment of the patients condition which may adversely affect decisions regarding the course of treatment including selection of medications administered to adjust fluid pressure.

SUMMARY OF THE INVENTION

The present invention relates to a mounting assembly on which pressure transducers can be mounted and used to accurately measure blood pressure within human or animal bodies. A preferred embodiment utilizes a light source on the mounting assembly that emits light that is directed by the user at an object to accurately position pressure transducers, which are positioned in a fixed relationship relative to the light source. As the transducers are, for many applications, aligned with a horizontal plane extending through the middle of the patient's heart, the light source can be directed by the user at the patient's heart to provide the necessary alignment.

Currently, the user simply aligns the transducer with the patient's body using his or her eye. However for a large number of patients and operating conditions, for every inch of misplacement of the transducer relative to the mid-heart plane, there is a difference in measured pressure in the range of 2–9 mm of mercury. The present invention is used to prevent the inaccuracies associated with this procedure to provide a more dependable and reproducible measurement of arterial or fluid pressure.

A preferred embodiment of the invention uses a light weight battery powered laser mounted on a molded plastic assembly as a light source. The plastic assembly is mountable on a standard IV pole and has a number of receiving members or connectors on which disposable pressure transducers are mounted.

The system can use a photodetector or light sensor to sense whether the beam of light emitted by the laser is directed at the desired location. The sensor can be positioned on the patient by the user and is connected by wire or wireless remote to an alarm or indicator circuit mounted on the plate or frame that houses the laser. The sensor can also be mounted on the frame and used with a reflector located on the patient. An audible alarm or light indicator mounted on the frame can be used to signal the user that the patient or the transducer has moved out of position and requiring realignment of the patient relative to the transducer.

A circuit controlling operation of the laser can include switches to provide for continuous, periodically pulsed or manual operation of the light source.

Manually operated knobs can be incorporated into the mounting frame to level the frame relative to a horizontal plane. Standard levels can be included in the frame so that the user can usually verify that the frame is level.

The above and other features of the invention including various novel details of construction and combinations of parts will now be more particularly described with reference to the accompanying drawings and pointed out in the claims. It will be understood that the particular transducer mounting plate embodying the invention is shown by way of illustration and not as a limitation of the invention. The principles and features of this invention may be employed and varied in numerous embodiments without departing from the scope of the invention.

DETAILED DESCRIPTION OF THE INVENTION

Conventionally, pressure transducers are usually mounted on a support plate, which is attached to the I.V. pole. The support plate has a level indication, a line on the front face of the plate, which is aligned with the level of the patient's heart so that the transducers can obtain an accurate absolute measurement of the pressure. Typically in operation, the user must lower his head to the level of the level indication and then visually align it with a region on the patient's side that corresponds to the approximate mid-level of the heart. This mode of operation presents a number of problems. First, in the close quarters of the usual operating room, many times there is insufficient space next to the I.V. pole for the user to perform the visual alignment. Moreover, even if this can be performed, the visual alignment technique is subject to inaccuracies arising out of improper lining up of the level indication, which may be four feet or more from the patient. Finally, if the support plate should become jarred or misaligned during operation or if the patient is moved, there is no way to confirm its proper alignment from the standing position or from the other side of the patient.

Figure 1:
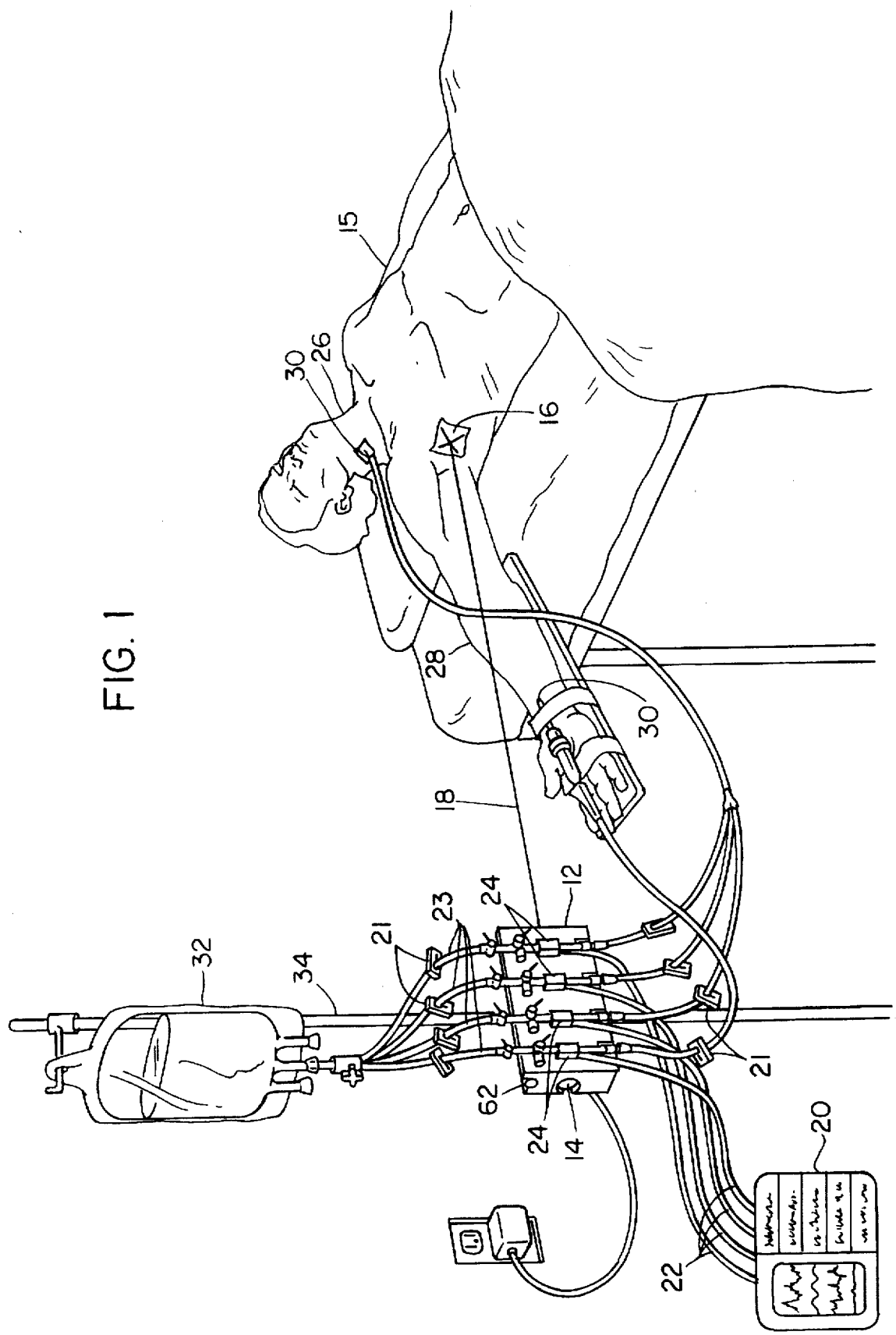
FIG. 1 is a schematic view of the pressure transducers, associated devices, and the transducer mounting plate of the present invention in relation to a patient.

Turning now to the drawings, an inventive pressure transducer mounting plate 12 and the general configuration for monitoring blood pressure of a patient 15 using one or more pressure transducers 24 is shown in FIG. 1. More specifically, an I.V. bag 32 containing saline solution is hung from an I.V. pole 34. The flow of the saline solution is provided to the patient via saline tubes 23. On these tubes, fluid flow restricters 21 are placed so that the flow level can be controlled. Also in line, between the patient 15 and the I.V. bag 32, transducers 24 is positioned connecting the saline tube 23, I.V. side, to the saline tube 23, on the patient side of the transducers. Each transducer 24 is electrically connected to a blood pressure monitor 20 via connecting wires 22 so that the pressure monitored by each transducer 24 can be displayed to the user. The patient side of the saline tubes 23 are then placed in fluid communication with the patient via catheters 30, which are inserted at various locations including the neck 26 or arm 28 to monitor pressure at the different locations.

The transducers 24, configured as described above, are capable of monitoring blood pressure based upon the principle that the pressure of the saline solution in the saline tube 23 on patient side fluctuates as a function of the blood pressure at the vascular position in which the catheter 30 is lodged. More specifically, the hemodynamic pressures generated by the pumping action of the patient's heart are transmitted through the blood within the patient's body, through the catheter 30, and into the saline tubes 23.

Each of the transducers 24 are detachably mounted on the mounting plate 12. The mounting plate 12 itself is then detachably mounted to the I.V. pole 34.

A light source 14, such as a laser, is encased in the mounting plate 12 and generates a beam of light directed along an optical path 18 to a desired location 16 on the patient 15. Further, the mounting plate 12 contains an integral spirit level 62, i.e., an arcuate liquid filled tube containing an air bubble, for confirming that the mounting plate 12 is level. Consequently, by first leveling the mounting plate 12 utilizing the spirit level 62 and then checking the location of the beam on light on the patient 15, the relative height of the mounting plate, and thus the transducers 24, can be determined.

Figure 2:
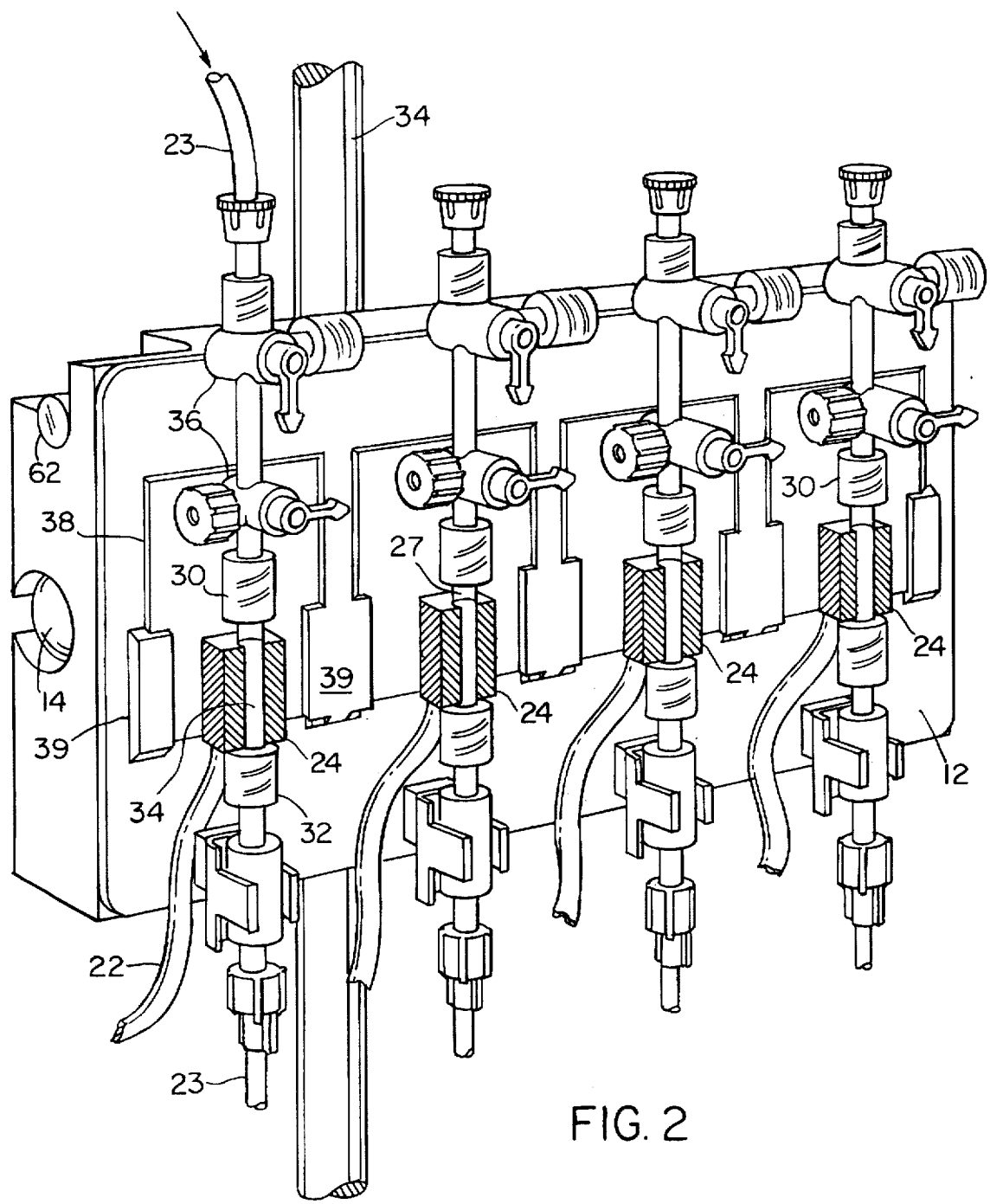
FIG. 2 is a perspective view of the pressure transducers on the mounting plate.

Turning now to FIG. 2, a more detailed perspective view of the transducer mounting plate 12 is illustrated. The mounting plate 12 is provided with mechanical connections capable of being connected to the I.V. pole 34. The transducers 24 each comprise a fluid connection inlet port 30 for connecting to the saline tube 23, I.V. bag side. A fluid connection outlet port 32 then connects to the saline tube 23, patient side. Connecting the inlet and outlet ports is a duct 34 housed within each transducer 24. The saline solution within this duct 34 has a pressure which pulsates in response to the blood pressure of the blood vessel in which the corresponding catheter 30 is inserted. A transducer circuit is in the transducer and in fluid communication with this duct. The transducer circuit includes a plate across on electrical assembly which generates an electrical signal that is a function of the pressure of the saline solution. A number of commercially available transducers can be used with the present invention. The each transducer 24 can be isolated from the saline solution source or the patient, or interconnected with other sources, by flow valves 36.

The each transducer 24 and its associated flow valves 36, fluid connection inlet port 30, and fluid connection outlet port 32 are mounted to a back plate 38. This back plate is slidably inserted into a pair flanges 39 formed on front face of the mounting plate 12. Finally, the connecting wire 22 provides an electrical connection to the blood pressure monitor 20 so that the electrical power is supplied to each transducer 24 and impulses generated by the transducer circuits can be transmitted to the monitor 20.

Figure 3:
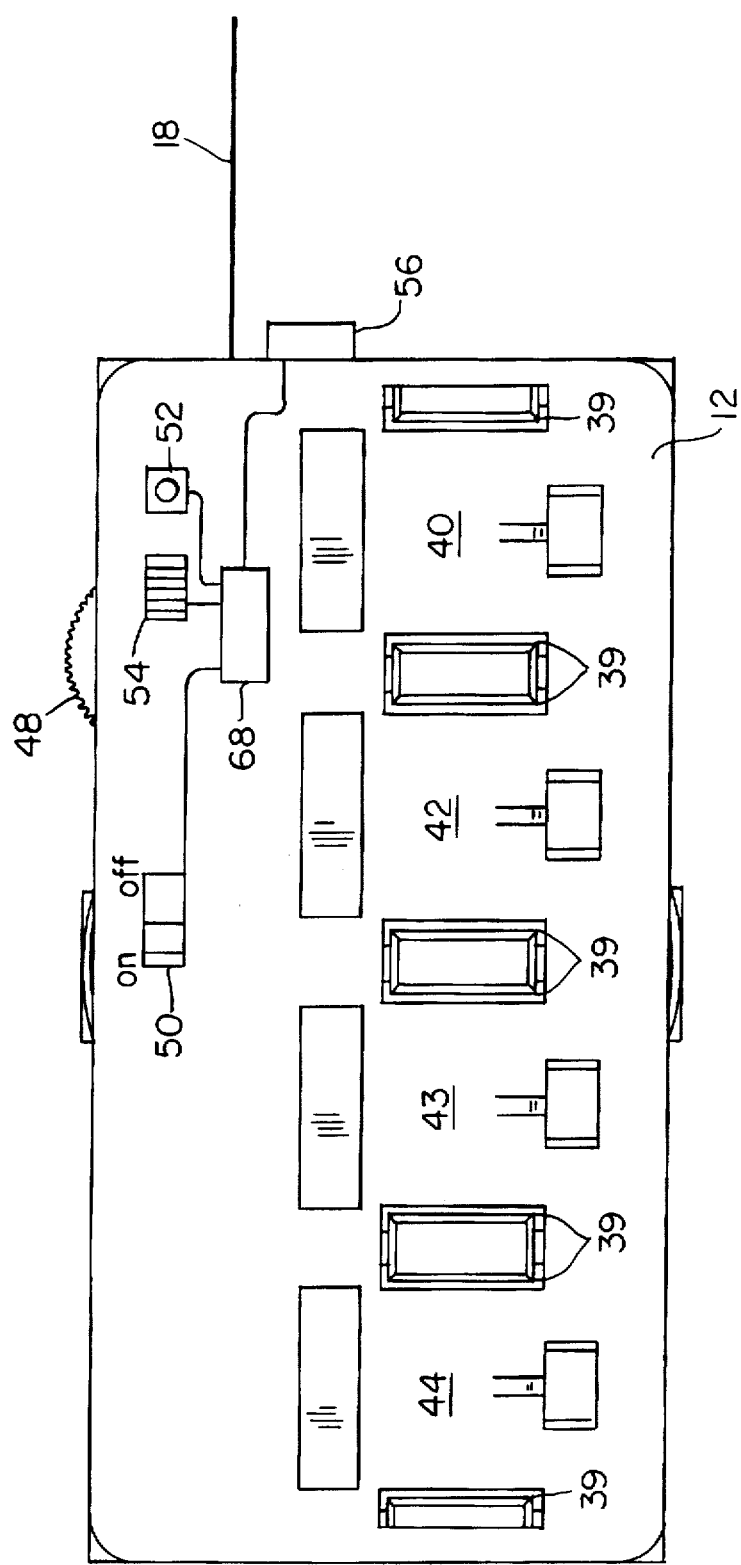
FIG. 3 is front view of the mounting plate.

FIG. 3 is a front view of the transducer mounting plate 12 without any transducers mounted to it. The front of the transducer plate 12 is provided with four regions 40, 42, 43, 44 for mounting four different pressure transducers via the flanges 39, or alternatively by an adhesive.

The mounting plate 12 can include a sensor 56 for detecting misalignment of the optical path 18 with the desired location 16. The sensor 56 can measure light returning from a reflector positioned at 16. Alternatively, the sensor 56 can be positioned at the location 16. A driver 68 monitors the response of the sensor 56 and then activates a light indicator 52 and/or audible alarm 54 to provide a warning to a user that the mounting plate 12 is misaligned. Further, sensors can be placed in the spirit levels 60, 62 and their outputs can be provided to the driver 68 to also provide a warning if the mounting plate is not level. A switch 50 can select continuous, intermittent or manual operation of the light source and the driver 68. A manual knob 48 can be used to level the mounting plate 12 relative to the horizontal plane.

Figure 4:
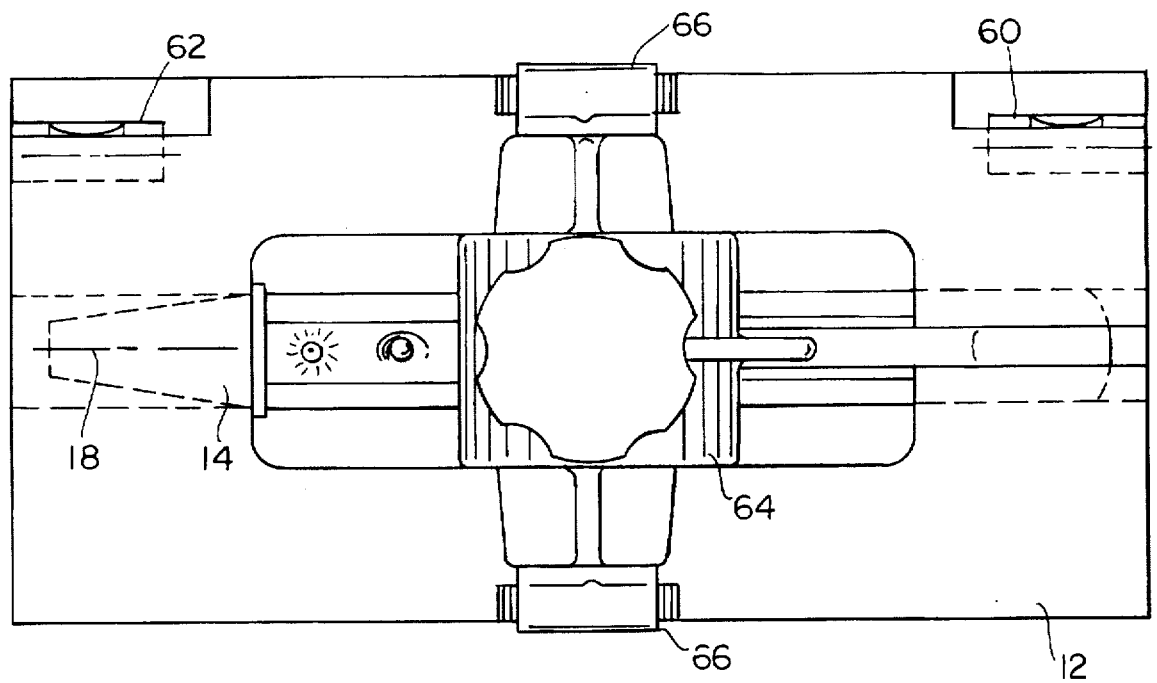
FIG. 4 is a rear view of the mounting plate.

FIG. 4 is a rear view of the transducer mounting plate 12. Here, two liquid tube spirit levels 60, 62 are provided at opposite lateral ends of the mounting plate 12 so that the plate, and consequently, the transducers themselves, can be leveled from a standing position. Further, a 0.5–5 mW laser pointer 14 generates a collimated beam of light parallel to the level line of the level tubes along optical path 18. Mounting bracket 64 connects the plate 12 via a spring metal tabs 66.

Figure 5:
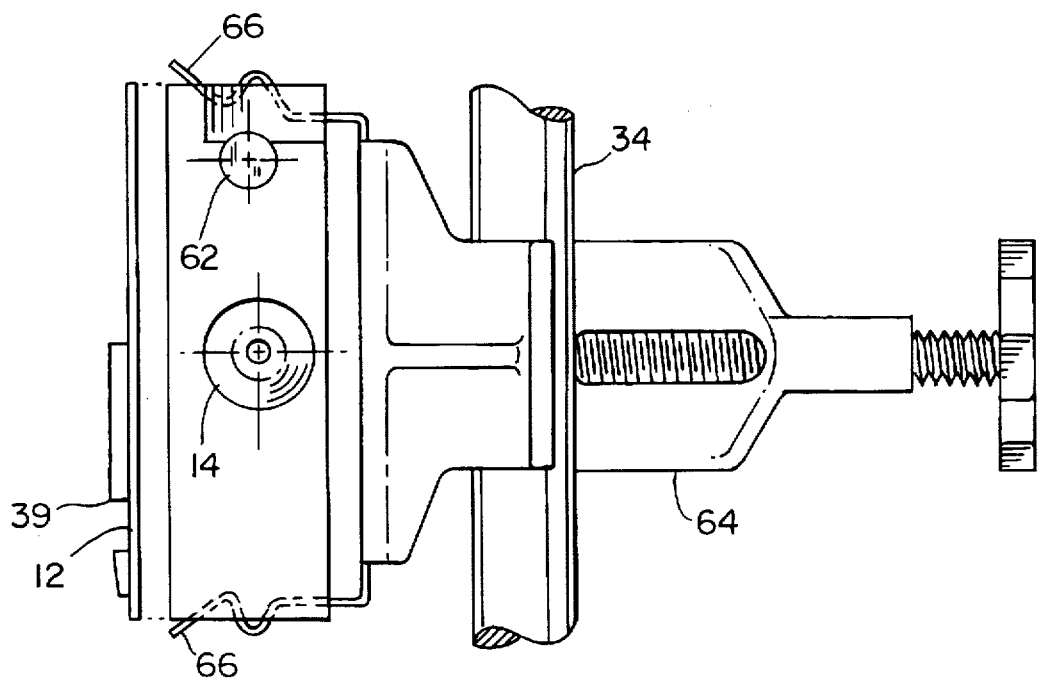
FIG. 5 is a side cross-sectional view of the mounting plate.

Finally, FIG. 5 illustrates a cross-sectional side view showing the laser pointer 14 disposed below the liquid level tube 62. Projecting from the front plate are flanges 39 for securing the back plates, which support the transducers. Extending from the rear of the transducer plate, the I.V. pole clamp 64 is attachable to the I.V. pole 34.

In operation of the present invention, the transducer plate 12 is first leveled using the level tubes 60, 62. This can be easily accomplished from the standing position while rotating the transducer plate. Once the transducer plate has been leveled, its vertical location relative to the patient's heart can be determined by viewing the point of light generated by the laser 14 on the patient's side 15. When this point of light is shining on the patient's side at the vertical position of the patient's heart, the transducers 24 of the transducer plate are properly positioned. As a result, not only can the alignment of the transducers be performed without squatting next to the I.V. pole, but the proper alignment of the transducer mounting plate 12 can be quickly confirmed during operation by simply inspecting the status of the level tubes and then the position of the light spot of the patient's side.

The transducers 24 are used to measure standard arterial pressure, pulmonary artery pressure, occluded pulmonary pressure, right atrial/central venous pressure, and left atrial/ pressure, for example. These measurements are commonly used to diagnosis the patient's condition and determine what medications and how much of these should be administered to the patient. The user can inject medications directly into the lines used to monitor fluid pressure in many applications.

Equivalents

Those skilled in the art will know or be able to ascertain using no more than routine experimentation, many equivalents to the specific embodiments of the invention described herein.

These and all other equivalents are intended to be encompassed by the following claims.

What is claimed is:

1. An optical positioning system for a bodily fluid pressure transducer comprising:

a light source for directing light along an optical path onto a patient's body;

a frame on which the light source is mounted, the frame having a connector to mount a fluid pressure transducer in a fixed orientation relative to the optical path;

a sensor adapted to be positioned relative to the patient's body to sense light emitted by the light source that is directed along the optical path; and an indicator for indicating a change in the light detected by the sensor.

2. The optical positioning system of claim 1 wherein the light source is a laser.

3. The optical positioning system of claim 1 further comprising a levelor mounted on the frame to indicate the orientation of the transducer connector relative to a horizontal plane.

4. The optical positioning system of claim 1 wherein the frame comprises a molded plastic.

5. The optical positioning system of claim 1 further comprising a battery electrically connected to the light source for supplying power to the light source.

6. The optical positioning system of claim 1 further comprising a plurality of fluid pressure transducers mounted on the frame with a plurality of connectors.

7. The optical positioning system of claim 1 wherein the sensor is positioned on the optical path between the light source and the patient's body.

8. The optical positioning system of claim 1 wherein the sensor is positioned on the frame.

9. A method of optically positioning a bodily fluid pressure transducer comprising:

providing a light source positioned relative to the transducer and a light sensor, the light sensor being positioned relative to a patient's body;

introducing a catheter into a body lumen, the catheter providing fluid communication between a position within the lumen and the transducer;

directing light from the light source along an optical path onto the light sensor;

sensing light that is directed towards the patient's body with the light sensor to identify a position of the transducer relative to the patient's body; and measuring fluid pressure with the transducer that is in a fixed orientation relative to the optical path.

10. The method claim 9 wherein the step of providing the light source further comprises providing a laser.

11. The method of claim 9 further comprising leveling a frame on which the fluid pressure transducer is mounted to define the orientation of the transducer relative to a horizontal plane.

12. The method of claim 11 further comprising providing a frame of molded plastic.

13. The method of claim 11 further comprising supplying power to the light source with a battery.

14. The method of claim 9 further comprising reflecting light emitted by the light source with a reflector toward the sensor.

15. An optical positioning system for a bodily fluid pressure transducer comprising:

a light source for directing light along an optical path onto a patient's body;

a frame on which the light source is mounted, the frame having a connector to mount a fluid pressure transducer in a fixed orientation relative to the optical path;

a sensor adapted to be positioned relative to the patient's body to sense light emitted by the source that is directed along the optical path;

an indicator for indicating a change in the light detected by the sensor;

a fluid pressure transducer mounted on the frame; and a catheter adapted to be positioned within the patient's body, the catheter providing fluid pressure coupling between the transducer and a position within the patient's body.

16. The optical positioning system of claim 15 wherein the light source is a laser.

17. The optical positioning system of claim 15 further comprising a levelor mounted on the frame to indicate the orientation of the transducer connector relative to a horizontal plane.

18. The optical positioning system of claim 15 wherein the frame comprises a molded plastic.

19. The optical positioning system of claim 15 further comprising a battery electrically connected to the light source for supplying power to the light source.

20. The optical positioning system of claim 15 further comprising an alarm that is connected to the sensor to indicate repositioning of the patient's body relative to the transducer.

21. An optical positioning system for a bodily fluid pressure transducer comprising:

a light source for directing light along an optical path onto a patient's body;

a plurality of fluid pressure transducers;

a frame on which the light source is mounted, the frame having a connector to mount the plurality of fluid pressure transducers in a fixed orientation relative to the optical path;

a sensor adapted to be positioned relative to the patient's body to sense light emitted by the source; and an indicator for indicating a change in the light detected by the sensor.

22. The optical positioning system of claim 21 wherein the light source is a laser.

23. The optical positioning system of claim 21 further comprising a levelor mounted on the frame to indicate the orientation of the connector relative to a horizontal plane.

24. The optical positioning system of claim 21 wherein the frame comprises a molded plastic.

25. The optical positioning system of claim 21 further comprising a battery that is electrically connected to the light source for supplying power to the light source.

26. The optical positioning system of claim 21 further comprising a reflector to reflect light emitted by the light source.

27. The optical positioning system of claim 21 further comprising a plurality fluid tubes in fluid communication between each transducer and separate locations.

* * * * *